Figure 1:
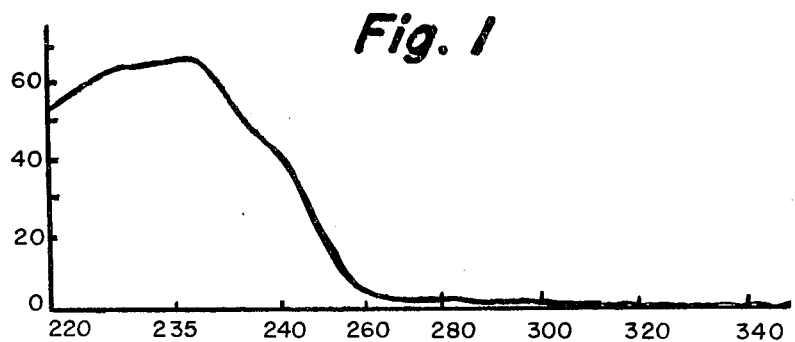

United States Patent [19]

Osono et al.

[11] 3,959,252

[45] May 25, 1976

[54] ALKAMOYL-JOSAMYCINS

[75] Inventors: Takashi Osono; Kiruko Moriyama; Keisuke Murakami; Hamao Umezawa, all of Tokyo, Japan

[73] Assignee: Yamanouchi Pharmaceutical Co., Ltd., Japan

[22] Filed: Aug. 21, 1972

[21] Appl. No.: 282,013

Related U.S. Application Data

[63] Continuation-in-part of Ser. No. 811,346, March 28, 1969, abandoned.

[30] Foreign Application Priority Data

Mar. 29, 1968 Japan.................................. 43-20381
Mar. 29, 1968 Japan.................................. 43-20382

[52] U.S. Cl....................... 260/210 AB; 260/210 R; 424/181

[51] Int. Cl............................................ C07c 129/18
[58] Field of Search............................. 260/210 AB

[56] References Cited

UNITED STATES PATENTS 3,535,309   10/1970   Hata et al..................... 260/210 AB Primary Examiner—Johnnie R. Brown
Attorney, Agent, or Firm—Wenderoth, Lind & Ponack

[57] ABSTRACT

Alkanoyl-josamycins having no bitter taste, in which at least one of the two secondary hydroxyl groups of Josamycin is acylated (introduction of alkanoyl group). The compounds have the same pharmaceutical effect as Josamycin which is effective in inhibiting the growth of Gram-positive bacteria.

12 Claims, 13 Drawing Figures

ALKAMOYL-JOSAMYCINS

This application is a continuation-in-part of application Ser. No. 811,346 filed Mar. 28, 1969, now abandoned.

This invention relates to alkanoyl-josamycins having no bitter taste in which at least one of the two secondary hydroxyl groups of Josamycin is acylated (hereinafter "acylate", "acylating" or "acylation" means to introduce alkanoyl group), and to the preparation thereof. [Josamycin is an antibiotic having properties inherent to macrolide antibiotics, which has been obtained by cultivating *Streptomyces narbonensis var. josamyceticus*, ATCC No. 17835, picked up from soil in Japan. A U.S Pat. No. 3,636,197, a Canadian Pat. No. 782,571 and French Pat. No. M-4385 have already been granted on Josamycin. Josamycin, in its base form, has been described as having the following properties: colorless needle crystals; melting point of 130°–133°C (uncorr.); molecular weight of 828.02, $pk_a'$ of 7.1 when titrated in aqueous methanol; specific rotation, $[\alpha]_D^{25}$ of $-70°$ ($c = 1\%$, in ethanol); ultraviolet absorption maximum at 232 m$\mu$ ($E_{1cm}^{1\%}$ 320) in methanol, and at 232 m$\mu$ ($E_{1cm}^{1\%}$ 325) in a 1/1000N aqueous hydrochloric acid solution; infrared absorption bands, when mixed with potassium bromide, at 3480, 2960, 2930, 2880 (shoulder), 1734, 1627, 1452, 1374, 1297, 1234, 1165, 1120, 1080, 1050, 1020, 995, 936, 916, 855 and 837 cm$^{-1}$, easily soluble in acidic water, methanol, ethanol, chloroform, ethyl acetate, and acetone; soluble in benzene, ether and carbon tetrachloride; slightly soluble in water, petroleum ether, ligroin, and n-hexane; elemental analysis of C = 60.63%, H = 8.49%, N = 1.77% and O = 28.75%; and a molecular formula of $C_{42}H_{69}NO_{15}$.]

The structural formula of the alkanoyl josamycins of this invention is as follows:

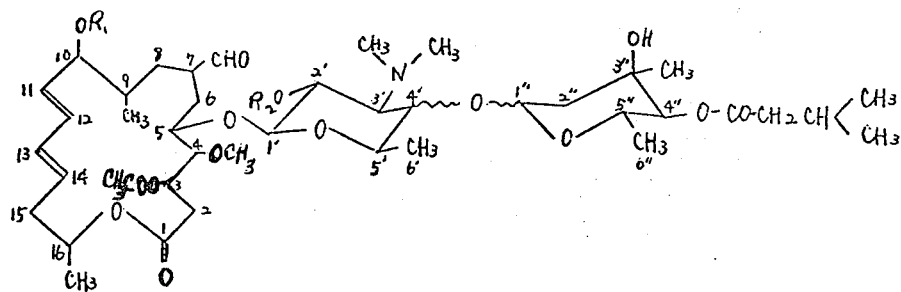

wherein $R_1$ and $R_2$ each represents hydrogen atom or a lower alkanoyl group, with proviso that $R_1$ and $R_2$ cannot be hydrogen atoms at the same time.

As mentioned above, Josamycin has one tertiary hydroxyl group on 3''-position, two secondary hydroxyl groups on 10- and 2'-positions and one acetoxy group on 3-position in the molecule. Josamycin, as the base or in the form of acid addition salts, such as hydrochloride, sulfate, tartrate, etc., is a useful medicament for the treatment of infections by Gram-positive bacteria. Thus, it inhibits the growth of such bacteria, e.g. staphylococci, at a concentration of 0.2 to 1.5μg/ml and also inhibits the growth of staphylococci resistant to streptothricin, telomycin, streptomycin, chloramphenicol, or penicillin. Josamycin and its acid-addition salts are thus particularly useful inter alia in combating infections in warm-blooded animals, due to staphylococci, e.g. *Staphylococcus aureus* (Smith) and to other infection-producing microorganisms.

However, Josamycin has a very bitter taste which constitutes a difficulty for oral administration. When Josamycin is administered orally, for example, in the form of tablets, the tablets must be coated with sugar or gelatin for masking the bitter taste.

According to the present invention, the bitter taste of Josamycin is removed by acylation. More precisely, when Josamycin is reacted with an organic carboxylic acid or its reactive derivative, used as the acylating agent, only the secondary hydroxyl groups of Josamycin are acylated on the 10- and 2'-positions; when the acylation of Josamycin is effected using about the equimolar amount of an acylating agent, a 2'-lower alkanoyl Josamycin is obtained (this compound may also be referred to as "monoacyl-josamycin-1"); when the acylation is effected under a basic reaction condition using more than the double equimolar amount of an acylating agent, a 10,2'-diloweralkanoyl Josamycin is obtained; when a diacyl-josamycin so obtained is hydrolyzed, another 10-lower alkanoyl Josamycin which is different from the monoacyl-josamycin-1 in respect of the position of the acylated hydroxyl group (this compound may also be referred to as "monoacyl-josamycin-2") is obtained; and all these acylated compounds have no bitter taste.

The difference in the position of the acylated hydroxyl group between monoacyl-josamycin-1 and monoacyl-josamycin-2 is proved by their physical properties. For instance, monoacetyl-josamycin-1 has a melting point of 182°–183°C and an Rf value (by thin-layer chromatography) of 0.50, while monoacetyl-josamycin-2 has a melting point of 128°–131°C and an Rf value of 0.58. They show depression of the melting point in a mixed examination. (It is of note that the Rf value of Josamycin in the same system is 0.46.) These two compounds are confirmed both to be a monoacetylated Josamycin, by quantitative analysis of acetyl group.

As examples of the compounds of this invention, the following can be mentioned: monoacetyl-josamycin-1, monoacetyl-josamycin-2, diacetyl-josamycin, monopropionyl-josamycin-1, monopropionyl-josamycin-2, dipropionyl-josamycin, monisovaleryl-josamycin-1, monoisovaleryl-josamycin-2, diisovaleryl-josamycin, etc., Thus, lower alkanoyl josamycins are exemplified.

To prepare a monoacyl-josamycin-1, the reaction of Josamycin with about the equimolar amount of an organic carboxylic acid or its reactive derivative, used as the acylating agent, can be carried out in an organic solvent such as a lower alcohol, ethyl acetate, acetone or the like. To obtain a diacyl-josamycin, the reaction of Josamycin with more than double equimolar amount of an acylating agent under a basic reaction condition can be carried out, for example, in the presence of pyridine, quinoline or the like. Though these acylation reactions progress smoothly at room temperature, they may be accelerated by heating. To prepare a monoacyl-josamycin-2, the hydrolysis of the corresponding diacyl-josamycin can be carried out in an organic solvent containing water (preferably containing 10 – 50% of water), such as aqueous methanol, aqueous ethanol, aqueous isopropanol, aqueous acetone, aqueous methylethylketone, aqueous dioxane, aqueous dimethylformamide, etc. This hydrolysis reaction is promoted by heating or by the addition of a basic reagent such as sodium carbonate, ammonia or the like, or an acidic reagent such as hydrochloric acid or the like. The product can easily be isolated because it usually precipitates in the reaction mixture as crystal. If desired, however, it can be isolated by extraction with a suitable organic solvent from the reaction mixture followed by concentrating the extract obtained under reduced pressure.

Among the products thus obtained there are some differences on melting point and optical rotation owing to the difference of number, nature of the lower alkanoyl groups and the position which Josamycin bond with the said groups, but there is no significant changes on ultra violet absorption and infra-red absorption spectra.

Figure 2:
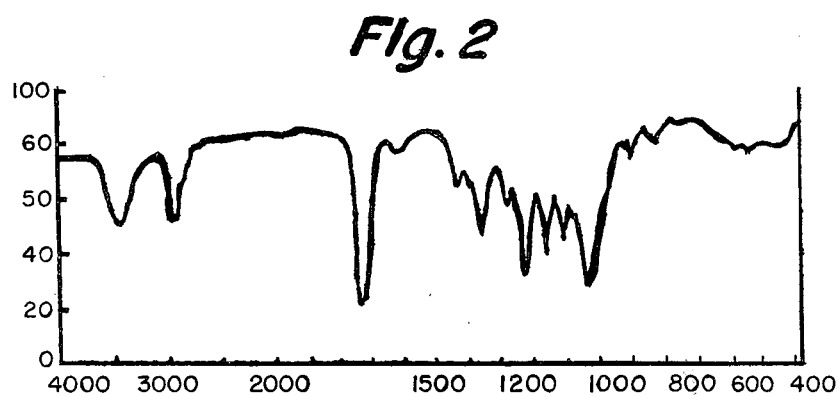

Ultra violet and infra-red absorption spectra of 2'-acetyl-josamycin which is typical lower alkanoyl-josamycin are shown in FIGS. 1 and 2.

Ultra violet absorption maximum of each product appears at 232 m$\mu$. On all products, absorption bands in the infra-red region of the spectrum in the form of KBr tablet at the following frequencies expressed in reciprocal centimeters: 3510, 2980-2720, 1740, 1460, 1375, 1235, 1190-1180, 1125, 1085, 1058.

As the organic carboxylic acids usable as acylating agent according to the present invention, there can be mentioned, for example, acetic acid, propionic acid, butyric acid, isovaleric acid, etc. Reactive derivatives of acid are, for example, acid anhydride, acid halogenide and the like.

Procedures for the preparation of the compounds of this invention will be further illustrated below.

To demonstrate the improvement brought about by the compounds of this invention, comparative tests on the bitter taste and on the antibacterial activity were effected between Josamycin and acetyl-josamycins, i.e., monoacetyl-josamycin-1, monoacetyl-josamycin-2 and diacetyl-josamycin.

1. The bitter taste

Experimental procedure: Bitterness of Josamycin, monoacetyl-josamycin-1, monoacetyl-josamycin-2 and diacetyl-josamycin was tested by blindfolded adults (male 8, female 4), by tasting. The results obtained are shown in the following Table I:

Table I

|  | Very bitter | Bitter | Slightly bitter | Scarcely bitter | Free from bitterness |
|---|---|---|---|---|---|
| Josamycin | 11 | 1 | — | — | — |
| Monoacetyl-josamycin-1 | — | — | 1 | 1 | 10 |
| Monoacetyl-josamycin-2 | — | — | — | 1 | 11 |
| Diacetyl-josamycin | — | — | — | — | 12 |

2. Antibacterial actvity a. in vitro

Experimental procedure: Minimum inhibitory concentrations (MIC) were determined as to Josamycin, monoacetyl-josamycin-1, monoacetyl-josamycin-2 and diacetyl-josamycin, according to usual agar dilution method on nutrient agar. The results are shown in the following Table II:

Table II

| Organism | Minimum Inhibitory Concentrations of Josamycin and Acetylated Josamycins (in meg/ml*) | | | |
|---|---|---|---|---|
|  | Josamycin | Monoacetyl-josamycin-1 | Monoacetyl-josamycin-2 | diacetyl-josamycin |
| *Staphylococcus aureus* FDA 209P | 0.39 | 0.39 | 0.39 | 0.39 |
| FDA 209P Smith | 0.39 | 0.39 | 0.39 | 0.39 |
| " PC, SM, TC, EM, SA resistant | >100 | >100 | >100 | >100 |
| " PC, CP, TC, SA resistant | 0.78 | 0.78 | 0.78 | 0.78 |
| *Bacillus subtilis* ATCC 6635 | 0.39 | 0.39 | 0.39 | 0.39 |
| Mycobacterium 607 | 3.1 | 3.1 | 3.1 | 3.1 |
| *Escherichia coli* PCI 602 | >100 | >100 | >100 | >100 |
| *Salmonella typhi* H 901W | >100 | >100 | >100 | >100 |
| *Shigella flexneri* 2a 1675 | 50 | 50 | 50 | 50 |

PC: penicillin, SM: streptomycin, TC: tetracycline,
EM:erythromycin, CP: chloramphenicol, SA: sulfa drugs
*The amounts of acetylated Josamycins are represented by those of Josamycin equivalent thereto.

b. in vivo i. Protection of mice from subcutaneous Staphylococcal infection.

Experimental procedure: Groups of 5 mice were inoculated subcutaneously in the back with $10^8$ cells (in 0.1 ml volume) of *Staphylococcus aureus* No. 226 strain. Immediately after the infection, Josamycin or monoacetyl-josamycin-2 was administered orally. To the control group, no medicament was administered. After 48 hours, the animals were killed. The skin of the back of each mouse was cut open, and the size of subcutaneous abscess was measured. The results are shown in the following Table III:

Table III

|  | Dose (mg/kg) | Size of abscess (mm$^2$) |
|---|---|---|
| Control | — | 88.2 |
| Josamycin | 200 | 4.19 |
| Josamycin | 50 | 21.2 |

Table III-continued

| | Dose (mg/kg) | Size of abscess (mm²) |
|---|---|---|
| Monoacetyl-josamycin-2 | 200 | 0.64 |

*The dose of monoacetyl-josamycin-2 is shown by the amount of Josamycin equivalent thereto.

ii. Protection of mice from systemic staphylococcal infection

Experimental procedure: Group of 5 mice were inoculated intraperitoneally with 1000 MLD (containing 5% of mucin added) of Staphylococcus aureus Smith. Immediately after the infection, a single dose of each antibiotic was given orally. The survival of mice after 7 days was observed. The group for control (10 mice) was given no antibiotic. The results are shown in the following Table IV:

Table IV

| Antibiotic | Route of administration | Dose (mg/kg) | Number of mice | Survival on 7th day |
|---|---|---|---|---|
| Josamycin | oral | 500 | 5 | 5 |
| " | " | 150 | 5 | 2 |
| " | " | 50 | 5 | 0 |
| Monoacetyl-josamycin-2 | " | 500* | 5 | 5 |
| " | " | 150* | 5 | 3 |
| " | " | 50* | 5 | 0 |
| none | — | — | 10 | 0 |

*The dose of monoacetyl-josamycin-2 is shown by the amount of Josamycin equivalent thereto.

The toxicities of the compounds of this invention were tested in mice, using monoacetyl-josamycin-1, monoacetyl-josamycin-2, and diacetyl-josamycin as being representative:

To male mice of ddN strain, weighing from 18 to 20 g, was given orally a single dose of 2g/kg of monoacetyl-josamycin-1, monoacetyl-josamycin-2 or diacetyl-josamycin. The mice were observed for 7 days. All the animals survived with no sign of toxicity, and no histological change was found on autopsy. Thus, these derivatives of Josamycin were proved to be of low toxicity.

The new compounds of this invention have the same utility as the known Josamycin as described supra and are usually administered orally, as a preparation in the form, for example, of tablet, powder, granule, syrup, chewable tablet, capsule, etc. Since the compounds of this invention have no bitter taste, it is not necessary on processing them into such preparations to apply a sugar or gelatin coating to the tablet or granule, or to correct or improve taste of the syrup.

The clinical dose of an alkanoyl-josamycin is about 1–3g per day, being calculated as Josamycin. The daily dose is divided into three to six portions, and the portion is administered at every 8 to 4 hours. The dose may vary depending on the age and physical condition of the patient (mammal).

EXAMPLE 1

1.0 gram (g) of Josamycin was dissolved in 2 milliliters (ml) of isopropanol by mild heating, and to the solution obtained 0.32 g of acetic anhydride was added. The reaction mixture was allowed to stand for a short time at room temperature, whereby needle crystals began to precipitate. The crystals were separated by filtration, and then recrystallized from 2 ml of 90% aqueous acetone to give 810 mg of monoacetyl-josamycin-1.

Physico-chemical properties of the monoacetyl-josamycin-1 thus obtained are as follows:
1. Color, crystal form, and melting point Colorless, needle crystal of m.p. 182°–183°C.
2. Elementary analysis as $C_{44}H_{71}NO_{16}$

| | C | H | N | $CH_3CO-$ |
|---|---|---|---|---|
| Calcd: | 60.74% | 8.23% | 1.61% | |
| Found: | 59.85% | 8.15% | 1.93% | 11.2% |

As the acetyl value of Josamycin containing one acetyl group is 6.18%, the compound obtained in this example has two acetyl groups.

3. Specific rotation $$[\alpha]_D^{25} = -86.0° \ (c = 1, CHCl_3)$$

4. pKa' less than 6 (measured in 40% aqueous methanol)
5. Absorption spectrum

Figure 3:
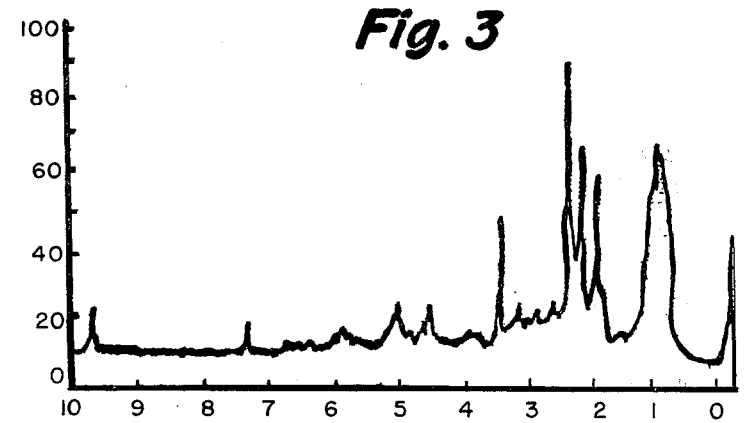

Ultraviolet-absorption spectrum of this compound, which was measured in methanol, is shown in FIG. 1, The maximum absorption ($E_{1cm}^{1\%}$ 343) appears at 232 m$\mu$. Infrared-absorption (KBr) of this compound is shown in FIG. 2. NMR spectrum of this compound, which was measured in heavy chloroform, is shown in FIG. 3.

6. Solubility

This compound is easily soluble in acetone, methylethylketone, chloroform, ethyl acetate and benzene, soluble in methanol and ethanol, and hardly soluble in water, petroleum ether and n-hexane.

7. Thin-layer chromatography

This compound was spotted on a thin-layer plate made of Alumina B-10 (a product of Wako Pure Chemical Co., for thin-layer chromatography use), and developed with a solvent system consisting of butyl acetate/methylethylketone/water (80 : 18 : 2). An Rf value of 0.50 was obtained. (The Rf value of Josamycin is 0.46.)

EXAMPLE 2

In 3 ml of ethyl acetate acetate was dissolved 1.0 g of Josamycin, and to the resulting solution was added 0.18 g of acetic anhydride. The reaction mixture was allowed to stand for 30 minutes at room temperature, whereby needle crystals precipitated. The crystals were separated by filtration, and then recrystallized from 2 ml of 90% aqueous acetone to give 780 mg of monoacetyl-josamycin-1 having a melting point of 182°–183°C.

EXAMPLE 3

In 50 ml of isopropanol were dissolved 5.0 g of crude Josamycin (of about 50% purity) by heating at 70°C, and the insoluble matter was removed from the resulting solution by filtration. To the filtrate obtained, 1.35 g of acetic anhydride were added. The reaction mixture was allowed to stand for 1 night at room temperature, and then was concentrated under reduced pressure into about 10 ml volume. The precipitates were separated by filtration, and then recrystallized from ethyl acetate to give 2.1 g of monoacetyl-josamycin-1 having a melting point of 182°–183°C.

EXAMPLE 4

To 0.5 g of Josamycin, 10 ml of acetic anhydried and 0.05 ml of pyridine were added. The reaction mixture was allowed to stand for 20 hours at room temperature, and then poured into 50 g of ice water. After 2 hours, the pH of the resulting mixture was adjusted to about 5 with 2N sodium hydroxide solution. The product thereby precipitated was separated by filtration, and recrystallized from 5 ml of 70% aqueous methanol to give 395 mg of diacetyl-josamycin as needle crystals.

Physico-chemical properties of the diacetyl-josamycin thus obtained are as follows:
1. Colorless, needle crystals, m.p. 152°–153°C.
2. Elementary analysis as $C_{46}H_{73}NO_{17}$

|  | C | H | N | $CH_3CO$ |
|---|---|---|---|---|
| Calcd: | 60.57% | 8.07% | 1.54% |  |
| Found: | 59.06% | 8.02% | 1.72% | 16.6% |

Figure 4:
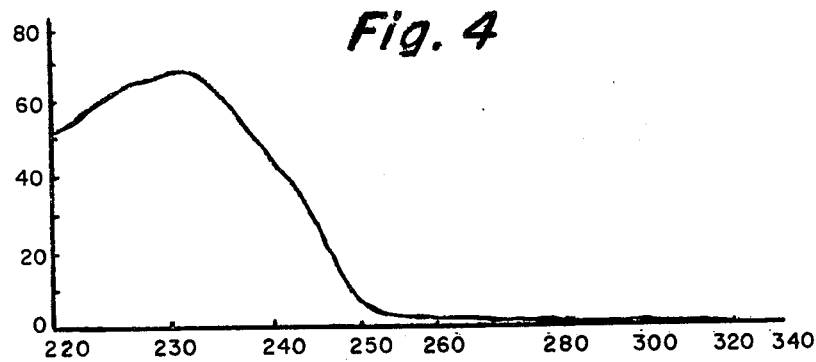
Figure 5:
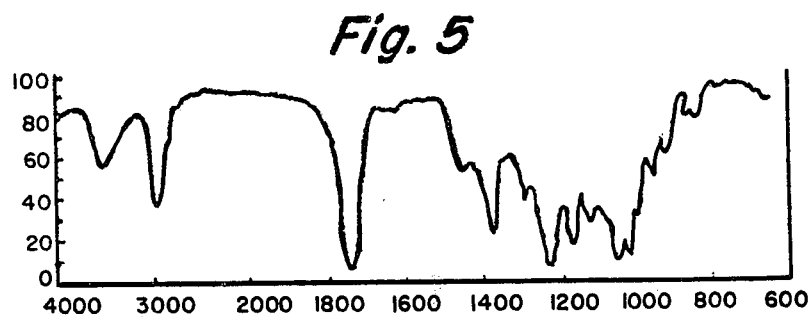
Figure 6:
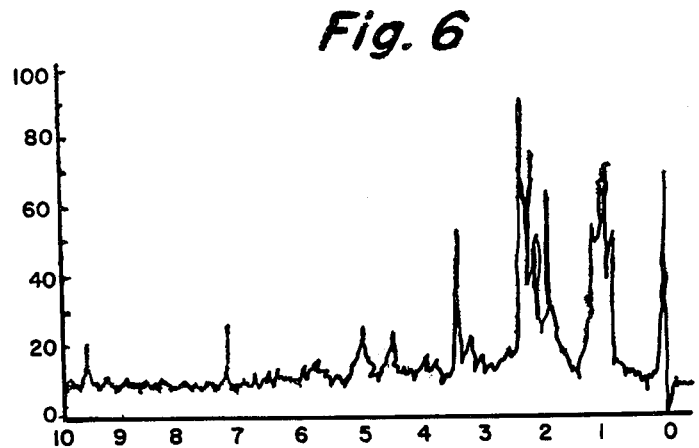

This indicates that this compound has three acetyl groups.
3. Specific rotation $[\alpha]_D^{25} = -.87.2°$ ($c = 1$, $CHCl_3$)
4. pKa' less than 6 (measured in 40% aqueous methanol)
5. Absorption spectrum Ultraviolet-absorption spectrum of this compound, which was measured in methanol, is shown in FIG. 4. The maximum absorption $E_{1cm}^{1\%}$ 333 appears at 232 m$\mu$. Infrared absorption (KBr) of this compound is shown in FIG. 5. The band at 3500 cm$^{-1}$ shows absorption by free tertiary hydroxyl group. NMR spectrum of this compound, which was measured in deutero chloroform, is shown in FIG. 6.
6. Solubility This compound is easily soluble in acetone, methylethylketone, chloroform, ethyl acetate and benzene, soluble in methanol and ethanol, and hardly soluble in water, petroleum and n-hexane.
7. Thin-layer chromatography This compound was spotted on a thin-layer plate made of Almina B-10 (a product of Wako Pure Chemical Co., for thin-layer chromatography use), and developed with a solvent system consisting of butyl acetate/methylethylketone/water (80 : 18 : 2). An Rf value of 0.64 was obtained. (The Rf value of Josamycin is 0.46.)

EXAMPLE 5

Figure 11:
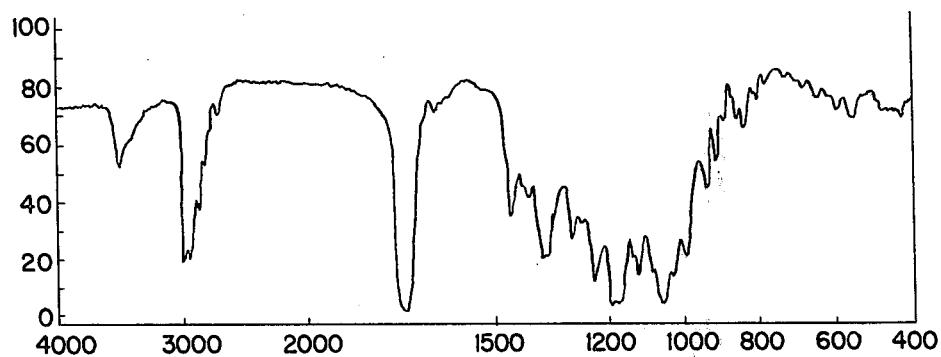

20 g of Josamycin were dissolved in 25 g of propionic anhydride, and to the solution obtained 0.1 ml of pyridine was added. The mixture was heated at 60°C for 5 hours, and then poured into 200 ml of ice water. After 2 hours, the pH of the resulting mixture was adjusted to about 5 with 2N sodium hydroxide solution. The white precipitates formed were separated by filtration, and then recrystallized from 70% aqueous methanol to give 1.01 g of dipropionyl-josamycin having a melting point of 130°–133°C. Infrared absorption spectrum (KBr) of this compound is shown in FIG. 11.

EXAMPLE 6

In 10 g of isovaleric anhydride 1.5 g of Josamycin were dissolved, and to the solution obtained 0.2 ml of pyridine was added The solution was heated at 65°C for 8 hours, and then poured into 200 ml of ice water. The pH of the resulting mixture was adjusted to and maintained for several hours at about 8, by adding 2N sodium hydroxide solution thereto while stirring. The reaction mixture was extracted twice with 200 ml each of ethyl acetate. The extract combined was washed with 2% sodium bicarbonate solution and water, and then dried over anhydrous sodium sulfate. The solvent was distilled off under reduced pressure to give 1.4 g of crystalline powder of diisovaleryl-josamycin having a melting point of 81°–86°C.

EXAMPLE 7

Figure 13:
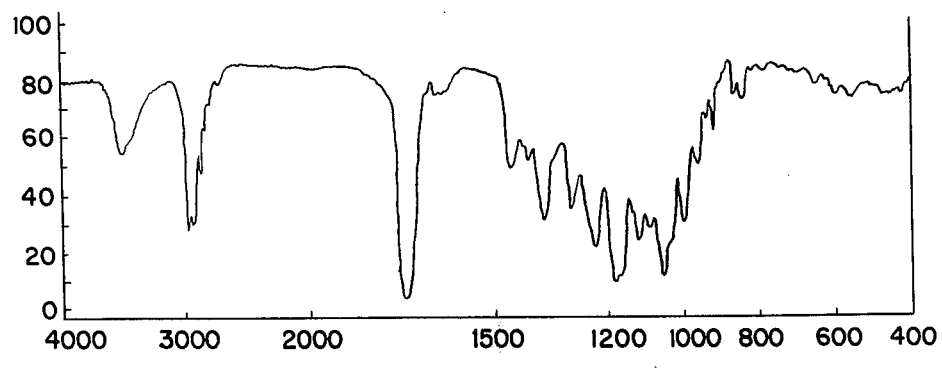

In 20 ml of toluene was dissolved 2.0 g of josamycin and to the solution obtained 2.0 g of n-butyric anhydride and 0.2 ml of pyridine were added. The resulting solution was heated to 65°C for 8 hours. The reaction mixture was washed with 100 ml of 2% sodium bicarbonate solution and 100 ml of water successively and dried over anhydrous sodium sulfate. The reaction mixture was condensed under reduced pressure and the residue obtained was dissolved in 20 ml of 80% aqueous methanol. The resulting solution was heated to 65°C for 8 hours and then condensed under reduced pressure. The residue obtained was recrystallized from 80% aqueous isopropanol to obtain 1.5 g of needle crystals of butyryl-josamycin-2 having an mp. 119° – 121°C. Infrared absorption spectrum (KBr) of this compound is shown in FIG. 13.

Elemental analysis as $C_{46}H_{75}NO_{16}$

|  | C(%) | H(%) | N(%) |
|---|---|---|---|
| Calcd. | 61.52 | 8.42 | 1.56 |
| Found | 61.44 | 8.37 | 1.62 |

Dibutyryl josamycin was also produced and exhibits the following properties:
1. Molecular formula, $C_{50}H_{81}NO_{17}$
2. Melting point, 113°–116°C
3. Crystal, colorless needles
4. Optical rotation, $[\alpha]_D^{25} = -37.2$ (C=0.5, $CHCl_3$)
5. U.V. ($E_{1\ cm}^{1\%}$ 299.5) $\lambda$ max. 232 m$\mu$
6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

Figure 12:
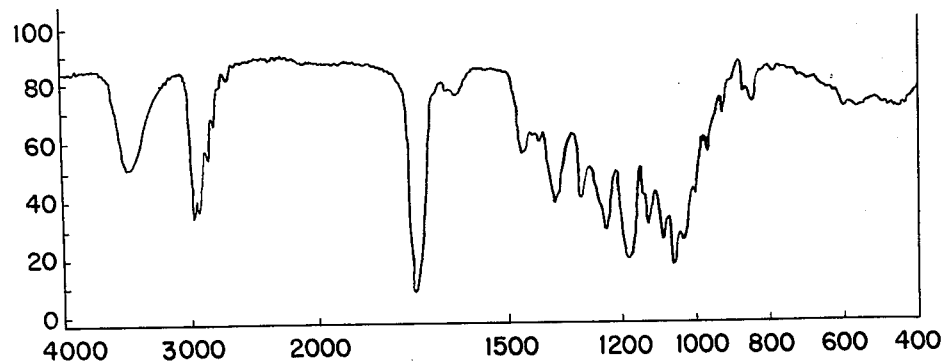

The infrared absorption spectrum (KBr) of this compound is shown in FIG. 12.

EXAMPLE 8

A. In 120 ml of acetic anhydride 6.0 g of Josamycin were dissolved, and to the solution obtained 3.0 ml of pyridine were added. The resulting solution was allowed to stand for 48 hours at room temperature, and then poured into 1 liter of ice water. The resulting mixture was allowed to stand for 2 hours, and then its pH was adjusted to about 5 with 2N sodium hydroxide solution. The white precipitates formed were separated by filtration, and recrystallized from 70% aqueous methanol to give 4.3 g of needle crystals of diacetyl-josamycin having a melting point of 152°–153°C.

b. In 120 ml of 80% aqueous methanol 4.1 g of diacetyl-josamycin obtained in (a) were dissolved, and the resulting solution was heated for 4 hours at 65°C. The insoluble matter formed as by-product in a very small quantity was removed by filtration, and then the methanol was distilled off. The white crystals precipitated were separated by filtration, and recrystallized from 80% aqueous methanol to give 3.0 g of colorless crystals of monoacetyl-josamycin-2.

Physico-chemical properties of the monoacetyl-josamycin-2 thus obtained are as follows:
1. Color, crystal form, and melting point Colorless, needle crystal m.p, 128°–131°C.
2. Elementary analysis as $C_{44}H_{71}NO_{16}$

|  | C | H | N | $CH_3CO-$ |
|---|---|---|---|---|
| Calcd: | 60.74% | 8.23% | 1.61% |  |
| Found: | 59.48% | 8.42% | 1.79% | 12.1% |

As mentioned above, the acetyl value of Josamycin containing one acetyl group is 6.18%, and therefore it is indicated that this compound has two acetyl groups in its molecule.

3. Specific rotation $[\alpha]_D^{25} = -51.1°c$ (c = 1, $CHCl_3$)

4. pKa 7.03 (measured in 40% aqueous methanol)
5. Absorption spectrum

Figure 7:
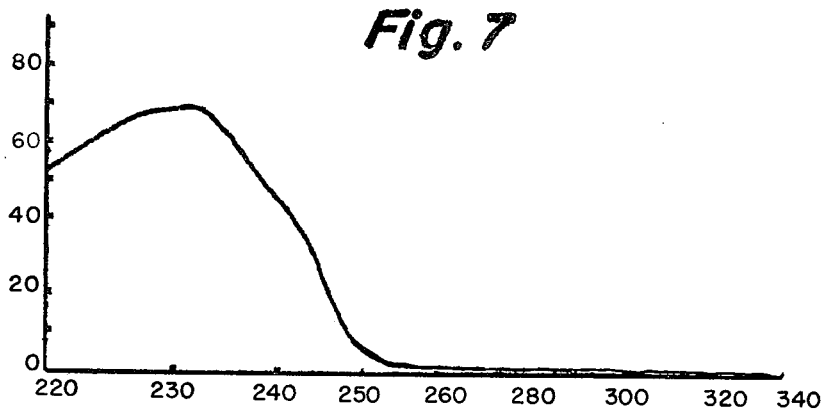
Figure 8:
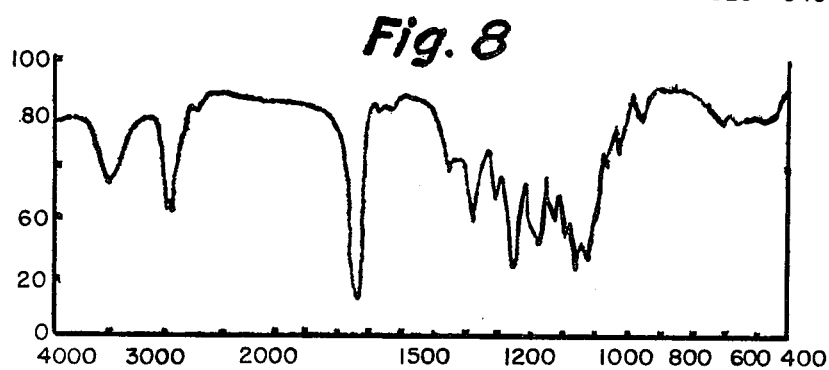
Figure 9:
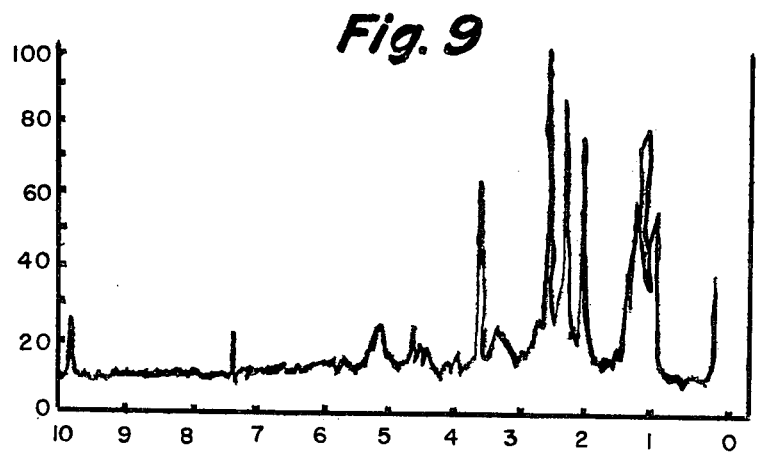

Ultraviolet-absorption spectrum of this compound, which was measured in methanol, is shown in FIG. 7. The maximum absorption ($E_{1cm}^{1\%}$ 338) appears at 232 mμ. Infrared absorption spectrum (KBr) of this compound is shown in FIG. 8. NMR spectrum of this compound, which was measured in heavy chloroform, is shown in FIG. 9.

6. Solubility

This compound is easily soluble in acetone, chloroform, methanol, ethyl acetate and ethylether, soluble in carbon tetrachloride, and hardly soluble in water, petroleum ether and n-hexane.

7. Thin-layer chromatography

This compound was spotted on a thin-layer plate made of Alumina B-10 (a product of Wako Pure Chemical Co., for thin-layer chromatography use), and developed with a solvent system consisting of butyl acetate/methylethylketone/water (80 : 18 : 2). An Rf value of 0.58 was obtained. (The Rf value of Josamycin is 0.46.)

EXAMPLE 9

In 150 ml of 70% aqueous acetone 5 g of diacetyl-josamycin were dissolved, and the solution obtained was heated for 8 hours at 60°C. The insoluble matter formed as by-product in a very small quantity was removed by filtration, and then the solvent was distilled off. The white crystalline precipitates obtained were recrystallized from 80% aqueous methanol to give 3.3g of monoacetyl-josamycin-2 having a melting point of 128°–131°C.

Figure 10:
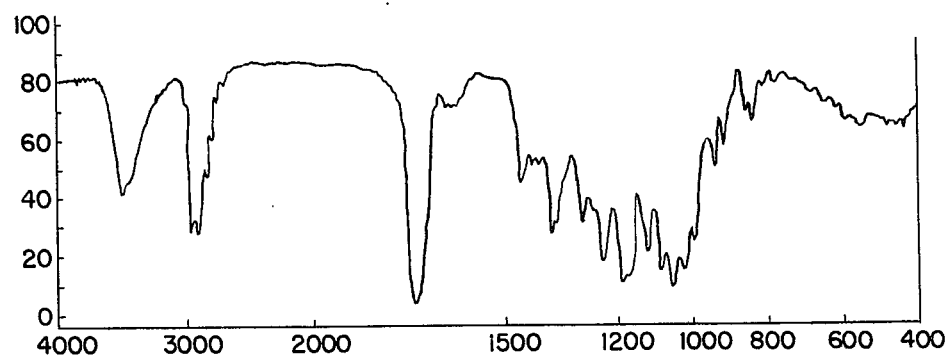

EXAMPLE 10 a. In 25 g of propionic anhydride 2.0 g of Josamycin were dissolved, and to the solution obtained 0.1 ml of pyridine was added. The resulting solution was heated for 5 hours at 60°C, and then poured into 200 ml of ice water. After 2 hours, the pH of the reaction mixture was adjusted to about 5 with 2N sodium hydroxide solution. The white precipitates formed were separated by filtration and recrystallized from 70% aqueous methanol to give 1.01 g of dipropionyl-josamycin having a melting point of 130°–133°C.

b. In 40 ml of 80% aqueous methanol 1.01 g of dipropionyl-josamycin obtained in (a) were dissolved, and the solution was heated for 5 hours at 65°C. The solvent was distilled off. The white crystalline powder thus obtained was dried under reduced pressure to give 0.85 g of monopropionyl-josamycin-2 having a melting point of 119°–124°C. Infrared absorption spectrum (KBr) of this compound is shown in FIG. 10.

EXAMPLE 11 a. In 10 g of isovaleric anhydride 1.5 g of Josamycin were dissolved, and to the solution obtained 0.2 ml of pyridine was added. The solution was heated for 8 hours at 65°C, and then poured into 200 ml of ice water. The pH of the resulting mixture was adjusted to about 8, by adding 2N sodium hydroxide solution thereto while stirring. The mixture was allowed to stand for several hours, with its pH maintained at about 8. The reaction mixture was then extracted twice with 200 ml each of ethyl acetate. The extract combined was washed with 2% sodium bicarbonate solution and water, and then dried over anhydrous sodium sulfate. The solvent was distilled off under reduced pressure to give 1.4 g of crystalline powder of diisovaleryl-josamycin having a melting point of 81°–86°C.

b. In 15 ml of 80% aqueous methanol 1.4 g of diisovaleryl-josamycin obtained in (a) were dissolved, and the solution obtained was heated for 30 hours at 65°C. The insoluble matter formed as by-product in a very small quantity was removed by filtration. From the filtrate, the solvent was distilled off under reduced pressure. The crystalline solid thus obtained was dried under reduced pressure to give 1.16 g of monoisovaleryl-josamycin-2 having a melting point of 69°–74°C.

EXAMPLE 12

Syrup formulation:

|  | grams |
|---|---|
| Monoacetyl-josamycin-2 | 4.0 (being calculated as Josamycin) |
| Polyoxyethylene monostearate 40 | 0.5 |
| Methyl p-hydroxybenzoate | 0.18 |
| Propyl p-hydroxybenzoate | 0.02 |
| Sodium carboxymethylcellulose | 0.5 |
| Sugar | 35.0 |
| Flavor | a proper quantity |
| Aq. dest. | the quantity to make the whole into 100 ml |

The syrup prepared according to this formulation contains 40 mg of monoacetyl-josamycin-2 in each 1 ml thereof.

EXAMPLE 13

Powder formulation:

|  | milligrams |
|---|---|
| Monacetyl-josamycin-2 | 400 (being calculated as Josamycin) |
| Calcium biphosphate | 300 |
| Lactose | 300 |

The above ingredients are triturated thoroughly until a very fine uniform powder is obtained.

We claim:
1. Lower alkanoyl-josamycins having the formula

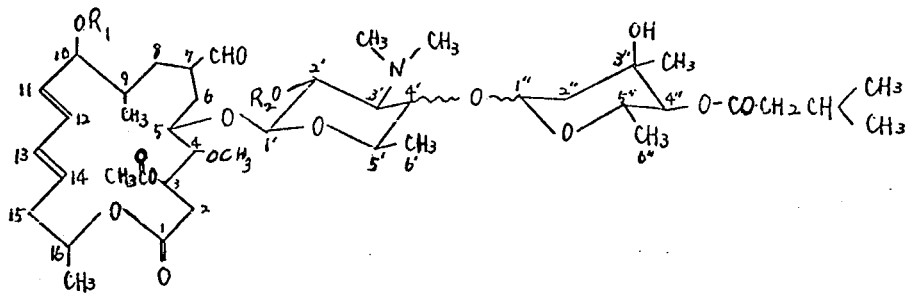

wherein $R_1$ and $R_2$ each represents hydrogen or a lower alkanoyl, with the proviso that $R_1$ and $R_2$ cannot be hydrogen at the same time.

2. Mono lower alkanoyl-josamycin as claimed in claim 1, wherein the said $R_1$ is a lower alkanoyl and the said $R_2$ is a hydrogen atom.

3. Di lower alkanoyl-josamycin as claimed in claim 1, wherein the said $R_1$ and $R_2$ are the same lower alkanoyl.

4. A compound according to claim 2, 10-acetyl-josamycin having the following properties:
 1. Molecular formula, $C_{44}H_{71}NO_{16}$
 2. Melting point, 128°–131°C
 3. Crystal, colorless needles
 4. Optical rotation, $[\alpha]_D^{25} = -51.1$ (C=1, CHCl$_3$)
 5. U.V. ($E_{1cm}^{1\%}$ 338) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

5. A compound according to claim 2, 10-propionyl-josamycin having the following properties:
 1. Molecular formula, $C_{45}H_{73}NO_{16}$
 2. Melting point, 119°–124°C
 3. Crystal, colorless needles
 4. Optical rotation, $[\alpha]_D^{25} = =52.2$ (C=1, CHCl$_3$)
 5. U.V. ($E_{1cm}^{1\%}$ 329) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

6. A compound according to claim 2, 10-butyryl-josamycin having the following properties:
 1. Molecular formula, $C_{46}H_{75}NO_{16}$
 2. Melting point, 126°–128°C
 3. Crystal, colorless needles
 4. Optical rotation, $[\alpha]_D^{25} = -54.9$ (C=1, CHCl$_3$)
 5. U.V. ($E_{1cm}^{1\%}$ 320) λ max. 232 mμ
 6. Characteristic infrared absorption in the form of KBr tablet at the following frequencies expressed in reciprocal centimeters: 3510, 2980-2720, 1460, 1375, 1235, 1190-1180, 1125, 1085, 1058.

7. A compound according to claim 2, 10-isovaleryl-josamycin having the following properties:
 1. Molecular formula, $C_{47}H_{77}NO_{16}$
 2. Melting point, 69°–74°C
 3. Crystal, colorless needles
 4. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

8. A compound according to claim 3, 2′-acetyl-josamycin having the following properties:
 1. Molecular formula, $C_{44}H_{71}NO_{16}$
 2. Melting point, 182°–183°C
 3. Crystal, colorless needles
 4. Optical rotation, $[\alpha]_D^{25} = 86.0$ (C=1, CHCl$_3$)
 5. U.V. ($E_{1cm}^{1\%}$ 338) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

9. A compound according to claim 3, 10,2′-diacetyl-josamycin having the following properties:
 1. Molecular formula, $C_{46}H_{73}NO_{17}$
 2. Melting point, 152°–153°C
 3. Crystal, colorless needles
 4. Optical rotation, $[\alpha]_D^{25} = -87.2$ (C=1, CHCl$_3$)
 5. U.V. ($E_{1cm}^{1\%} = 333$) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

10. A compound according to claim 3, 10,2′-dipropionyl-josamycin having the following properties:
 1. Molecular formula, $C_{48}H_{77}NO_{17}$
 2. Melting point 130°–133°C
 3. Crystal, colorless needles
 4. Optical rotation, $[\alpha]_D^{25} = -47.3$ (C=0.5, CHCl$_3$)
 5. U.V. ($E_{1cm}^{1\%}$ 320) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

11. A compound according to claim 3, 10,2′-dibutyryl-josamycin having the following properties:
 1. Molecular formula, $C_{50}H_{81}NO_{17}$
 2. Melting point, 113°–116°C
 3. Crystal, colorless needles
 4. Optical rotation, $[\alpha]_D^{25} = -37.2$ (C=0.5, CHCl$_3$)
 5. U.V. ($E_{1cm}^{1\%}$ 299.5) λ max. 232 mμ
 6. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

12. A compound according to claim 3, 10,2′-diisovaleryl-josaycin having the following Properties:
 1. Molecular formula, $C_{52}H_{85}NO_{17}$
 2. Melting point, 81°–86°C
 3. Crystal, colorless needles
 4. Characteristic infrared absorption in the form of KBr tablet at the following frequencies expressed in reciprocal centimeters: 3510, 2980-2720, 1740, 1460, 1375, 1235, 1190-1180, 1125, 1085, 1058.

* * * * *